United States Patent
Chang et al.

(10) Patent No.: US 12,104,161 B2
(45) Date of Patent: *Oct. 1, 2024

(54) **PRODUCTION OF SOLUBLE RECOMBINANT PROTEINS WITHOUT N-TERMINAL METHIONINE IN *E-COLI***

(71) Applicant: Fina BioSolutions, LLC, Rockville, MD (US)

(72) Inventors: Min-Ju Chang, Gaithersburg (CA); Natalia Oganesyan, North Potomac, MD (US); Andrew Lees, Silver Spring, MD (US)

(73) Assignee: Fina Biosolutions LLC, Rockville, MD (US)

( * ) Notice: Subject to any disclaimer, the term of this patent is extended or adjusted under 35 U.S.C. 154(b) by 749 days.

This patent is subject to a terminal disclaimer.

(21) Appl. No.: 17/371,449

(22) Filed: Jul. 9, 2021

(65) Prior Publication Data

US 2021/0348174 A1 Nov. 11, 2021

Related U.S. Application Data

(63) Continuation-in-part of application No. 16/819,775, filed on Mar. 16, 2020, now Pat. No. 11,060,123, which is a continuation of application No. 16/154,020, filed on Oct. 8, 2018, now Pat. No. 10,597,664, which is a continuation-in-part of application No. 15/114,642, filed as application No. PCT/US2015/014130 on Feb. 2, 2015, now Pat. No. 10,093,704.

(60) Provisional application No. 63/147,227, filed on Feb. 8, 2021, provisional application No. 61/934,377, filed on Jan. 31, 2014.

(51) Int. Cl.
| | | |
|---|---|---|
| C12N 15/70 | (2006.01) | |
| A61K 38/00 | (2006.01) | |
| A61K 47/60 | (2017.01) | |
| C07K 1/22 | (2006.01) | |
| C07K 14/235 | (2006.01) | |
| C07K 14/33 | (2006.01) | |
| C07K 14/34 | (2006.01) | |
| C12N 9/02 | (2006.01) | |
| C12N 9/06 | (2006.01) | |

(52) U.S. Cl.
CPC .............. *C12N 15/70* (2013.01); *A61K 47/60* (2017.08); *C07K 1/22* (2013.01); *C07K 14/235* (2013.01); *C07K 14/33* (2013.01); *C07K 14/34* (2013.01); *C12N 9/003* (2013.01); *C12N 9/0051* (2013.01); *A61K 38/00* (2013.01); *C12N 2830/30* (2013.01)

(58) Field of Classification Search
CPC .................................................. C12N 15/70
See application file for complete search history.

(56) References Cited

U.S. PATENT DOCUMENTS

| | | | |
|---|---|---|---|
| 9,238,817 B2 | 1/2016 | Ruddock | |
| 9,976,164 B2 | 5/2018 | Ruddock | |
| 10,597,664 B2 * | 3/2020 | Oganesyan | ............ C07K 14/34 |
| 11,060,123 B2 * | 7/2021 | Oganesyan | ............ C12P 21/02 |
| 2004/0043468 A1 | 3/2004 | Mauro | |
| 2004/0063187 A1 | 4/2004 | Roemisch | |
| 2006/0030022 A1 | 2/2006 | Beckwith | |
| 2007/0254334 A1 | 11/2007 | Beckwith | |
| 2011/0287443 A1 | 11/2011 | Retallack | |
| 2015/0184215 A1 | 7/2015 | Hsu | |

FOREIGN PATENT DOCUMENTS

| | | |
|---|---|---|
| JP | 2012-531198 | 12/2012 |
| JP | 2013-529064 | 7/2013 |
| WO | WO 2007/063129 | 6/2007 |
| WO | WO 2010/139858 | 12/2010 |
| WO | WO 2011/042516 | 4/2011 |
| WO | WO 2011/123139 | 10/2011 |
| WO | WO 2011/126811 | 10/2011 |
| WO | WO 2010/150230 | 12/2012 |
| WO | WO 2013/140335 | 9/2013 |
| WO | WO 2013/178974 | 12/2013 |

OTHER PUBLICATIONS

Examination Report for CN App. No. 201580018271.2 dated Jul. 9, 2019.
Examination Report for CN App. No. 201580018271.2 dated Jul. 9, 2019—translation.
Examination Report for EP App. No. 15 743 243.6 dated Jul. 29, 2019.
Examination Report for CA App. No. 2,938,251, dated May 25, 2017.
Examination Report for CA App. No. 2,938,251, dated Jul. 12, 2019.
CN Examination Report for CN Application No. 201580018271.2 dated Feb. 27, 2019.
CN Examination Report for CN Application No. 201580018271.2 dated Feb. 27, 2019 (translation).
Study of the expression and purification of the diphtheria toxin variant CRM197 and the properties thereof, Xiao Jiagaimei, China Master's Theses Full-text Database, *Volume of medical and health science and technology*, E059-231, published Oct. 15, 2012 (in Chinese).
Influence of the Reductase Deficient *Escherichia coli* on the Solubility of Recombinant Proteins Produced in It, Xiong Sheng et al., *Chinese Journal of Biotechnology*, vol. 19.6:686-691, published Nov. 30, 2003 (in Chinese).

(Continued)

*Primary Examiner* — Brian Gangle
*Assistant Examiner* — Lakia J Jackson-Tongue
(74) *Attorney, Agent, or Firm* — Remenick PLLC

(57) ABSTRACT

The present invention is directed to the cells, compositions and methods for the production of recombinant protein, wherein an f-met group on the 5'-terminus is enzymatically removed. In particular, the invention is directed to a production process for obtaining high levels of soluble recombinant $CRM_{197}$ protein from *E. coli*. Cells preferably contain one or more mutations of disulfide reductase genes, so that disulfide reductase activity is reduced. The invention also relates to purification method for $CRM_{197}$ as well as characterization of properly folded $CRM_{197}$ protein.

35 Claims, No Drawings

(56) References Cited

OTHER PUBLICATIONS

Soluble expression of recombinant human fibroblast growth factor-8a in *Escherichia coli*, Fu Can, *Journal of Heze University*, vol. 31:94-98, published Mar. 31, 2009 (in Chinese).
JPO Examination Report for JP 2016-567466 dated Mar. 14, 2019.
JPO Examination Report for JP 2016-567466 dated Mar. 14, 2019 (translation).
EPO Examination Report for EP 15 743 243.6 dated Nov. 28, 2018.
Tanito et al., Invest Ophthalmol Vis Sci., 2002; 43: 2392-2400.
EPO Examination Report for EP 15 743 243.6 dated Jun. 18, 2018.
Zhao et al., Chinese Journal of Cellular and Molecular Immunology, Nov. 2003;19(6):585-7. (Year: 2003).
JPO Examination Report for JP 2016-567466, dated Jul. 5, 2018.
JPO Examination Report for JP 2016-567466, dated Jul. 5, 2018 (Translation).
Ganesh P. Subedi et al., Overproduction of Anti-Tn Antibody MLS128 Single-Chain Fv Fragment in *Escherichia coli* cytoplasm using a novel pCold-PDI vector, Protein Expression and Purification 82:197-204 (2012).
Mirella D. Lorenzo et al., Heterologous Production of Functional Forms of Rhizopus oryzae Lipase in *Escherichia coli*, Applied and Environmental Microbiology, 71(12):8974-8977 (2005).
EPO Supplemental Search Report dated Oct. 10, 2017.
EPO Written Opinion dated Oct. 10, 2017.
JP Examination Report for JP 2016-567466, dated Sep. 4, 2017.
JP Examination Report for JP 2016-567466, dated Sep. 4, 2017 (English Translation).
T. Uchida et al., Diphtheria Toxin and Related Proteins, The Journal of Chemistry, 218(11):3838-44. 1973.
Xiong et al., World Journal of Gastroenterology 2005; 11(7):1077-1082.
Stefan et al., Journal of Bacteriology 156:245-252 (2010).
Mahamad et al., Applied Genetics and Molecular Biotechnology 100:6319-6330 (2016).
Levy et al., Protein Expression and Purification 23:338-347 (2001).
EP Application No. 15 74 3243 Search Report dated Jun. 26, 2017.
EP Application No. 15 74 3243 Provisional Opinion Accompanying Search Report dated Jun. 26, 2017.
CA Exam Report for CA App. No. 2938251. dated May 25. 2017.
AU Exam Report for PCT/US15/14130, dated Jun. 6, 2017.
AU Exam Report for PCT/US15/14130, dated Feb. 21, 2017.
NZ Exam Report for PCT/US15/14130, dated Apr. 24, 2017.
De Marco A "Strategies for successful recombinant expression of disulphide bond-dependent proteins in *Escherichia coli*" Microbial Cell Factories, vol. 8, No. 26, pp. 1-18.
Bessette PH et al. "Efficient folding of proteins with multiple disulphide bonds in *Escherichia col* cytoplasm" Proceedings of the National Academy of Sciences, vol. 96, No. 24 pp. 13703-13708.
Samuelson JC et al. "Disulfide-Bonded Protein Production in *E. coli*", Genetic Engineering & Biotechnology News, Tutorials, vol. 32, No. 3.
AU Exam Report for PCT/US15/14130, dated Mar. 31, 2017.
Aminian, M. et al., Protein Expression and Purification, 2007, vol. 51, pp. 170-178.
Cabiaux, V. et al., Molecular Microbiology, 1988, vol. 2, No. 3, pp. 339-346.
NZ Exam Report for PCT/US15/14130, dated Dec. 2, 2016.
Lobstein, J et al, "Shuffle, a novel *Escherichia coli* protein expression strain capable of correctly folding disulfide bonded proteins in its cytoplasm," Microbial Cell Factories, vol. 11, No. 753, DOI:10.1186/1475-2859-11-56.
PCT Search and Patentability Report for PCT/US15/14130, dated Apr. 29, 2015.
Examination Report for JP Application No. 2019-128165 dated Jun. 16, 2021.
Examination Report for JP Application No. 2019-128165 dated Jun. 16, 2021—Translation.
Examination Report for KR Application No. 10-2016-7023611 dated May 24, 2021 (not translated).
Examination Report for IN Application No. 201617026437 dated Aug. 28, 2020.
De Marco A "Strategies for successful recombinant expression of disulphide bond-dependent proteins in *Escherichia coli*" Microbial Cell Factories, vol. 8, No. 26, pp. 1-18 (2009).
Bessette PH et al. "Efficient folding of proteins with multiple disulphide bonds in *Escherichia coli* cytoplasm" Proceedings of the National Academy of Sciences, vol. 96, No. 24, pp. 13703-13708 (Nov. 1999).
Samuelson JC et al. "Disulfide-Bonded Protein Production in *E. coli*", Genetic Engineering & Biotechnology News, Tutorials, vol. 32, No. 3 (Feb. 2012).
Lobstein, J et al, "Shuffle, a novel *Escherichia coli* protein expression strain capable of correctly folding disulfide bonded proteins in its cytoplasm," Microbial Cell Factories, vol. 11, No. 753, DOI:10.1186/1475-2859-11-56 (2012).
*Seibutukogaku* (Biotechnology), 2013, 91(2): p. 96-100 (in Chinese).
Examination Report for JP Application No. 2019-128165 dated Aug. 26, 2020.
Examination Report for JP Application No. 2019-128165 dated Aug. 26, 2020 (translation).

\* cited by examiner

PRODUCTION OF SOLUBLE RECOMBINANT PROTEINS WITHOUT N-TERMINAL METHIONINE IN E-COLI

REFERENCE TO RELATED APPLICATIONS

This application is a continuation-in-part of U.S. application Ser. No. 16/819,775, filed Mar. 16, 2020, which issued as U.S. Pat. No. 11,060,123 on Jul. 13, 2021, which is a continuation of U.S. application Ser. No. 16/154,020 filed Oct. 88, 2018, which issued as U.S. Pat. No. 10,597,664 on Mar. 24, 2020, which is a continuation-in-part of U.S. application Ser. No. 15/114,642 filed Jul. 27, 2016, which issued as U.S. Pat. No. 10,093,704 on Oct. 9, 2018, which is a National Stage Application, under 35 U.S.C. § 371, of International Application No. PCT/US2015/14130 filed Feb. 2, 2015, which claims priority to U.S. application Ser. No. 16/819,775 filed Mar. 16, 2020; and claims priority to U.S. Provisional Application No. 63/147,227 filed Feb. 8, 2021, and International Application No. PCT/US2021/22126 filed Mar. 12, 2021, which claims priority to U.S. Provisional Application No. 63/152,954, filed Feb. 24, 2021, and U.S. Provisional Application No. 62/990,083 filed Mar. 16, 2020, the entirety of each of which is specifically incorporated by reference.

BACKGROUND

1. Field of the Invention

The invention is directed to methods and compositions for the expression and purification of products such as peptides and proteins in microorganisms. In particular, pre-products are expressed recombinantly, wherein the cytoplasm of the microorganism alters the expressed pre-products to produce products in a final or usable form. Alterations include shifting of the redox state of the cytoplasm and site directed cleavage and/or ligation.

2. Description of the Background

Diphtheria toxin (DT) is a proteinaceous exotoxin synthesized and secreted by pathogenic strains of *Corynebacterium diphtheriae*. These pathogenic strains contain a bacteriophage lysogen that carries the toxin gene. Diphtheria toxin is an ADP-ribosylating enzyme that is secreted as a proenzyme of 535 residues and processed by trypsin-like proteases with release of two fragments (A and B). Fragment A uses NAD as a substrate, catalyzing the cleavage of the N-glycosidic bond between the nicotinamide ring and the N-ribose and mediating the covalent transfer of the ADP-ribose (ADPRT activity) to the modified histidine 715 (diphthamide) of the elongation factor EF-2. This post-translational diphthamide modification inactivates EF-2, halting protein synthesis and resulting in cell death. The A fragment of DT (also named C domain) carries the catalytic active site and is the only fragment of the toxin required for the final step of intoxication. The R domain, carried on the B fragment, mediates binding to receptors on the host cell surface and the T domain, also carried on the B fragment, promotes the pH-dependent transfer of fragment A to the cytoplasm. An Arginine-rich disulfide-linked loop connects fragment A to fragment B (or domain C to domains TR). This inter-chain disulfide bond is the only covalent link between the two fragments after proteolytic cleavage of the chain at position 186. The isolation of various non-toxic and partially toxic immunologically cross-reacting forms of diphtheria toxins (CRMs or cross reacting materials) resulted in discovery of $CRM_{197}$ (Uchida et al., Journal of Biological Chemistry 248, 3845-3850, 1973; see also Giannini et al. Nucleic Acids Res. 1984 May 25; 12(10):4063-9). Preferably, CRMs can be of any size and composition that contain all or a portion of DT.

$CRM_{197}$ is an enzymatically inactive and nontoxic form of diphtheria toxin that contains a single amino acid substitution G52E. This mutation causes intrinsic flexibility of the active-site loop in front of the NAD-binding site and reduces the ability of $CRM_{197}$ to bind NAD and eliminates toxic properties of DT (Malito et al., Proc Natl Acad. Sci. USA 109(14):5229-342012) Like DT, $CRM_{197}$ has two disulfide bonds. One disulfide joins Cys186 to Cys201, linking fragment A to fragment B. A second disulfide bridge joins Cys461 to Cys471 within fragment B. Both DT and CRM197 have fragment A-associated nuclease activity (Bruce et al., Proc. Natl. Acad. Sci. USA 87, 2995-8, 1990).

$CRM_{197}$ is commonly used as the carrier protein for protein-carbohydrate and hapten-protein conjugates. As a carrier protein, $CRM_{197}$ has a number of advantages over diphtheria toxoid as well as other toxoid proteins, many of which have been documented (Shinefield Vaccine, 28:4335, 2010, Broker et al, Biologicals, 39:195 2011). For example, since $CRM_{197}$ is genetically detoxified, it retains a larger complement of lysines, which are used for conjugation but are blocked by chemical toxoiding. $CRM_{197}$ has proven to be an effective carrier protein for *Streptococcus pneumonia* capsular polysaccharides, as evidenced by the success of PREVNAR™ (Pfizer), a vaccine consisting of up to 13 capsular polysaccharides chemically linked to $CRM_{197}$. There is also evidence suggesting that compared with tetanus toxoid, there is less carrier-induced suppression of the immune response, especially when there are many individual polysaccharides linked to the same carrier protein.

$CRM_{197}$ and native DT have a similar affinity for the diphtheria toxin receptor (DTR), which has an identical amino acid sequence to the HB-EGF precursor pro-HB-EGF (Mitamura et al., J. Biol. Chem. 272(43):27084-90, 1997). $CRM_{197}$ binds to the soluble form of HB-EGF, as well as to the membrane form pro-HB-EGF, and inhibits HB-EGF mitotic action by preventing its binding to EGF receptor. Thus $CRM_{197}$ may also have a future role in cancer therapy (Miyamoto et al., Anticancer Res. November-December 27(6A):3713-21, 2007).

Although $CRM_{197}$ has been produced in the original host *Corynebacterium*, yields are low, typically <50 mg/L and, in addition, *Corynebacterium* growth is relatively slow as compared with, for example, *E. coli*. *Corynebacterium* strains have been engineered to produce $CRM_{197}$ at higher levels (e.g., see U.S. Pat. No. 5,614,382). $CRM_{197}$ has also been expressed in a strain of *Pseudomonas fluorescens* and expressed at high levels. However, production of $CRM_{197}$ in other strains would be advantageous such as strains at a BL1 level and strains that are inexpensive to culture and propagate. Production of $CRM_{197}$ in *E. coli* has mainly resulted in insoluble inclusion bodies (generally insoluble), which then requires a difficult refolding process, resulting in low yields.

*E. coli* is the widely used host to produce recombinant proteins for research and therapeutic purposes. Recombinant proteins can be expressed in *E. coli* cytoplasm or periplasm. Periplasm has oxidative environment therefore many recombinant proteins containing disulfide bonds are produced in the periplasm to ensure proper folding and solubility. The signal peptide that directs recombinant protein into periplasm is clipped off during the secretion process into the periplasm, resulting in production of protein with the native amino acid sequence. However, the translocation mechanisms that direct proteins to the periplasm have limited capacity and so periplasmic expression level of recombinant proteins is usually low. On the other hand, expression in *E. coli* cytoplasm can lead to grams of recombinant proteins per liter of cell culture. However, the *E. coli* cytoplasm has reducing environment, and recombinant proteins containing disulfide bonds are usually insoluble when expressed intracellularly. Another limitation to cytoplasmic recombinant protein expression in *E. coli* is that in order to initiate expression of recombinant protein in *E. coli* the coding sequence of the protein should start from ATG codon, which is translated to formyl-methionine (N-terminal methionine). During intracellular expression of recombinant protein, the N-terminal methionine is excised by endogenous *E. coli* methionine aminopeptidase (MAP). This process is not effective even if the size of the residue adjacent is optimal for cleavage due to overexpression of the protein and limited amount of MAP. Usually a substantial amount of purified recombinant protein contains methionine as a first amino acid, which is not a part of mature protein sequence. This is not desirable for the most of therapeutic proteins. The existing methods to ensure effective cleavage of formyl-methionine include treatment in vitro with recombinant MAP or adding MAP coding sequence to expression vector and co-express the MAP coding sequence with recombinant protein to increase MAP amount. Both approaches are time consuming and costly. Commercially available *E. coli* strains (e.g., Origami®, Shuffle®) with gor-/trx-mutations available from Millipore and New England Bio, respectively, can produce soluble, intracellular proteins containing disulfide bonds, but the cell strains are crippled and do not grow to a high density limiting production yield. Thus, while these strains are suitable for generating research material, their low growth levels make them difficult to use commercially. Thus, a need exists for strains that express high levels of properly folded proteins that do not contain an N-terminal methionine.

SUMMARY OF THE INVENTION

The present invention overcomes the problems and disadvantages associated with current strategies and designs and provide new compositions and methods for producing recombinant peptides and proteins.

One embodiment of the invention is directed to methods of producing recombinant peptides and proteins in bacteria comprising: expressing the protein from a recombinant cell containing an expression vector that encodes the protein sequence, wherein the recombinant cell has a reduced activity of one or more disulfide reductase enzymes, wherein the one or more disulfide reductase enzymes comprises one or more of an oxidoreductase, a dihydrofolate reductase, a thioredoxin reductase, or a glutathione reductase, wherein the reduced activity of one or more disulfide reductase enzymes results in a shift the redox status of the cytoplasm to a more oxidative state as compared to a recombinant cell that does not have reduced activity of one or more disulfide reductase enzymes, expressing a peptidase from the recombinant cell, which is either integrated into the genome of the host cell, or expressed recombinantly via an expression vector, that acts on the protein expressed and removes a formyl-methionine group from the N-portion of the protein; and isolating the protein. Peptidases that remove an N-terminal methionine include MAP, METAP1 (Methionine aminopeptidase 1), and METAP2 (Methionine aminopeptidase 2). Preferably the integrated gene or expression vector contains a ribosome binding site, an initiation codon, and an expression enhancer region. Preferably the recombinant cell has a reduced activity of only one disulfide reductase enzyme or a reduced activity of only two disulfide reductase enzymes. Preferably the recombinant cell is an *E. coli* cell or a derivative or strain of *E. coli*, and preferably the recombinant protein expressed comprises tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, Hemophilus influenzae protein D, Flagellin Fli C, Horseshoe crab Haemocyanin, and fragments, derivatives, and modifications thereof. Preferably the integrated gene and/or expression vector contains an inducible promoter for the peptidase, and expressing comprises inducing the inducible promoter with a first inducing agent and contains an expression vector that encodes the recombinant peptide or protein which may be inducible with a second inducing agent. Preferably the first and second inducing agents are the same, although they may be different. Preferably the first integrated gene or expression vector contains an inducible second promoter and expressing the peptidase comprises inducing the inducible second promoter with the first inducing agent. Preferably isolating comprises chromatography wherein the chromatography comprises a sulfate resin, a gel resin, an active sulfated resin, a phosphate resin, a heparin resin or a heparin-like resin. Preferably the isolated protein expressed is conjugated with polyethylene glycol and/or a derivative of polyethylene glycol or with a polymer such as, for example, a polysaccharide, a peptide, an antibody or portion of an antibody, a lipid, a fatty acid, or a combination thereof.

Another embodiment of the invention comprises methods of producing a peptide comprising: expressing the peptide with a formyl-methionine group at a N-terminus of the peptide from a recombinant cell containing an expression vector that encodes the peptide, wherein the recombinant cell has a reduced activity of one or more disulfide reductase enzymes and the expression vector contains a promoter functionally linked to a coding region of the peptide, wherein the reduced activity of one or more disulfide reductase enzymes results in a shift the redox status of the cytoplasm to a more oxidative state as compared to a recombinant cell that does not have reduced activity of one or more disulfide reductase enzymes, and expressing a peptidase from an integrated gene of a recombinant cell that acts on the peptide expressed and removes the formyl-methionine group from the N-terminus of the peptide; and isolating the peptide. Preferably the expression vector contains a ribosome binding site, an initiation codon, and an expression enhancer region. Preferably the recombinant cell has a reduced activity of only one disulfide reductase enzyme or only two disulfide reductase enzymes. Preferably the one or more disulfide reductase enzymes comprises one or more of an oxidoreductase, a dihydrofolate reductase, a thioredoxin reductase, or a glutathione reductase. Preferably the recombinant cell is an *E. coli* cell or a derivative or strain of *E. coli* and the peptide or protein comprises tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, Hemophilus influenzae protein D, Flagellin Fli C, Horseshoe crab Haemocyanin, and fragments, derivatives, and modifications thereof. Preferably the promoter is an inducible promoter and expressing comprises inducing the inducible promoter with an inducing agent. Preferably isolating comprises chromatography, wherein the chromatography comprises a sulfate resin, a gel resin, an active sulfated resin, a phosphate resin, a heparin resin or a heparin-like resin. Preferably the peptide isolated is conjugated with polyethylene glycol (PEG) and/or a derivative of PEG, or coupled to a polymer such as, for example, a polysaccharide, a peptide, an antibody or portion of an antibody, a lipid, a fatty acid, or a combination thereof.

Other embodiments and advantages of the invention are set forth in part in the description, which follows, and in part, may be obvious from this description, or may be learned from the practice of the invention.

DESCRIPTION OF THE INVENTION

Soluble, intact recombinant $CRM_{197}$ was first produced in protease-deficient *E. coli* (Bishai et. al 1987). However, the amount of protein production was very low. Subsequently, $CRM_{197}$ was produced in *E. coli* cells as inclusion bodies (Stefan A, et al. J Biotechnol. December 20; 156(4):245-52, 2010; International Application Publication No. WO 2011/126811, Chinese Patent Application No. 200610042194) or as soluble protein directed to the periplasm by signal peptide (International Application Publication No. WO 2011/042516). The periplasm of *E. coli* is an oxidizing environment that allows the formation of disulfide bonds. $CRM_{197}$ has two disulfide bonds that are probably important for the correct folding and function, and for protein solubility.

Uncleaved chains of soluble recombinant CRM protein can be rapidly produced intracellularly and in commercial quantities from microorganisms and thereafter isolated and/or purified in large quantities and remain soluble. CRM is soluble in phosphate buffered saline (PBS, pH 7.5) and other similar buffers, and without harsh treatments. However, these chains contain a formyl-methionine (f-met) at their N-terminus.

It has been surprisingly discovered that strains of microorganisms can be engineered that fulfill the goals of: (i) expression of soluble recombinant proteins containing disulfate bonds in the cytoplasm; and (ii) effectively removing formyl-methionine from the sensible recombinant protein sequence. Expression strain have been developed that produces a large quantity of properly folded protein without a formyl-methionine at the protein's N-terminus.

As a first step, the shift from reducing to oxidative cytoplasmic environment was achieved by deletion of a gene. This single mutation allows disulfate bonds to be formed in the cytoplasm and does not affect cells vitality resulting in high cell density growth. In addition, the BL21 gor-strain has an additional copy of an indigenous methionine aminopeptidase (MAP) gene. Peptidases that remove an N-terminal methionine include MAP, METAP1 (Methionine aminopeptidase 1), and METAP2 (Methionine aminopeptidase 2), all of which can be utilized. The coding sequence of *E. coli* MAP, optionally under control of inducible promoter, was inserted in the place of deleted Gor locus of BL21 gor- to prevent further disruption of the genome. Having inducible promoter allows initiate expression of additional MAP gene at selected time and only when more MAP is needed to effectively remove formyl-methionine from overexpressed recombinant protein (which may be integrated or expressed from an expression vector). The tac-promoter was utilized as an inducible promoter for MAP. Thus, expression of the second MAP will start at the same time as expression of the recombinant protein, for example, when using IPTG to induce expression. Other inducible promoters for MAP expression can be used. *E. coli* (BL21 Gor/met) strain is capable of producing soluble disulfide bonds containing proteins intracellularly in grams quantity per liter of cell culture and sufficiently remove N-terminal methionine, resulting in the expression of native recombinant protein sequence.

Insertion deletion was used to replace Gor with sequences of chloramphenicol genes in between two Flipase recognition sites. Once bacteria with insertion deletion was identified by being Chloramphenicol resistant, the flipase gene in a plasmid would was introduced to remove the chloramphenicol gene. The final bacterial strain has one flipase recognition site remained and the Gor gene deletion.

Preferred CRM proteins produced are full length or partial regions such as, for example, peptides, single or multiple domains or epitopes, and any specific region expressed from native CRM coding sequences including CRM sequences that have been modified with one or more deletions, substitution and/or additions (e.g. conservative or non-conservative), and CRM sequences that have been modified with additional sequences (e.g., one or more promoters, start codons, and translation factor, ribosome or polymerase binding sites) that promote expression in a host organism. A preferred CRM protein is $CRM_{197}$. Preferred is expression of CRM protein that is soluble and not otherwise bound as insoluble inclusion bodies of the cell. Preferred expression systems for the expression and production of CRM proteins include microorganisms with an intracellular oxidative state. Preferred expression systems may be recombinant or native eukaryotic or prokaryotic cells wherein recombinant cells include cells that contain a non-native CRM coding sequence. Preferred prokaryotic cells are strains of *E. coli* or another bacterial strain that contains one or more genetic alterations (e.g., one or more deletions or mutations). Preferably the one or more genetic alterations shift the redox state of the cytoplasm of the cell to a more oxidative state, as compared to wild-type, for example as disclosed in U.S. Pat. No. 7,410,788 (which is incorporated by reference). Alterations preferably reduce the activity of one or more disulfide reductase genes and/or other genes that reduce the oxidative state of the cytoplasm. Preferably, reduced activity is due to non-expression or reduced expression of one, two or multiple disulfide reductase or other genes, or one or more mutations that reduce activity of one or more expressed disulfide reductase proteins or other proteins. Preferred strains of microbial cells (e.g., recombinant, engineered or native eukaryotic or prokaryotic cells) have increased abilities to produce natively folded proteins containing disulfide bonds yet remain as functional proteins. The method of the invention produces quantities of CRM proteins containing full, truncated or modified CRM amino acid sequences (which may be integrated or expressed from an expression vector). Quantities of CRM protein produced according to the invention are surprising such as, for example, 600 mg or more of CRM protein per liter of bacterial cell culture.

One embodiment of the invention is directed to methods for the production of large quantities of protein, and preferably $CRM_{197}$, from an *E. coli* host cells wherein an f-met that is present at the N-terminus of the protein is enzymatically removed. Production quantities are typically quantified as mg/L of bacterial cell culture. Protein production, according to the methods of the invention, is 200 mg/L or more, 300 mg/L or more, 400 mg/L or more, 500 mg/L or more, 600 mg/L or more, 700 mg/L or more, 800 mg/L or more, 900 mg/L or more, 1,000 mg/L or more, 1,500 mg/L or more, or 2,000 mg/L or more. Protein expressed according to the invention include full length and truncated proteins, as well as modified amino acid sequences of the protein. Modifications include one or more of conservative amino acid deletions, substitution and/or additions. A conservative modification is one that maintains the functional activity and/or immunogenicity of the molecule, although the activity and/or immunogenicity may be increased or decreased. Examples of conservative modifications include, but are not limited to amino acid modifications (e.g., single, double and otherwise short amino acid additions, deletions and/or substitutions), modifications outside of the active or functional sequence, residues that are accessible for conjugation in forming a vaccine, modifications due to serotype variations, modifications that increase immunogenicity or increase conjugation efficiency, modification that do not substantially alter binding to heparin, modifications that maintain proper folding or three dimensional structure, and/or modifications that do not significantly alter immunogenicity of the protein or the portions of the protein that provide protective immunity.

Recombinant cells that are used in the method of the invention are preferably E. coli bacteria and, preferably, E. coli that are genetically engineered to shift the redox state of the cytoplasm to a more oxidative state such as, for example, by mutation of one or more disulfide reductase genes such as, for example, an oxidoreductase, a dihydrofolate reductase, a thioredoxin reductase, a glutamate cysteine lyase, a disulfide reductase, a protein reductase, and/or a glutathione reductase. Preferably one or more disulfide reductase genes are mutated and rendered non-functional or marginally functional such that the redox state of the cytoplasm of the cell is shifted to a more oxidative state as compared to wild type. Oxidative protein folding involves the formation and isomerization of disulfide bridges and plays a key role in the stability and solubility of many proteins including CRM197. Formation and the breakage of disulfide bridges is generally catalyzed by thiol-disulfide oxidoreductases. These enzymes are characterized by one or more Trx folds that consist of a four-stranded β-sheet surrounded by three α-helices, with a CXXC redox active-site motif. The assembly of various Trx modules has been used to build the different thiol oxidoreductases found in prokaryotic and in eukaryotic organisms. In the bacterial periplasm, the proteins are kept in the appropriate oxidation state by a combined action of the couples DsbB-DsbA and DsbD-DsbC/DsbE/DsbG (Inaba 2009, Gruber et al, 2006). Many protein expression systems are well known in the art and commercially available.

Especially preferred microbes include E. coli expression strains, for example, chemically competent E. coli K12 cells engineered to form disulfide bonded proteins in the cytoplasm (e.g., ORIGAMI™ (EMD Millipore) and SHUFFLE™ (New England Biolabs)). Other strains and types of cells and other E. coli strains with enhanced oxidative redox state also may be used. For example, ORIGAMI™ 2 host strains are K-12 derivatives that have mutations in both the thioredoxin reductase (trxB) and glutathione reductase (gor) genes, which greatly enhance disulfide bond formation in the E. coli cytoplasm. These strains are kanamycin sensitive; like the original Origami strains, the gor mutation is still selected for by tetracycline. To reduce the possibility of disulfide bond formation between molecules, strains containing mutations in trxB and gor are recommended only for the expression of proteins that require disulfide bond formation for proper folding. SHUFFLE™ cells are chemically competent E. coli K12 cells engineered to form proteins containing disulfide bonds in the cytoplasm. Preferably these cells contain mutations in trxB and gor and cytoplasmic chaperon disulfide bond isomerase DsbC (fhuA2 [lon] ompT ahpC gal λatt::pNEB3-r1-cDsbC (SpecR, lacI$^q$) ΔtrxB sulA$_{11}$ R(mcr-73::miniTn10—Tet$^S$)2 [dcm]R(zgb-210::Tn10—Tet$^S$) endA1 Δgor Δ(mcrC-mrr)114::IS10). Also preferably, cells are suitable for T7 promoter driven protein expression and of the genotype F' lac, pro, lacIQ/Δ(ara-leu)7697 araD139 fhuA2 lacZ::T7 gene1 Δ(phoA)PvuII phoR ahpC* galE (or U) galK λatt::pNEB3-r1-cDsbC (Spec$^R$, lacI$^q$) ΔtrxB rpsL150(Str$^R$) Δgor Δ(malF)3. SHUFFLE™ strains expresses constitutively a chromosomal copy of the disufide bond isomerase DsbC. DsbC promotes the correction of mis-oxidized proteins into their correct form. Cytoplasmic DsbC is also a chaperone that can assist in the folding of proteins that do not require disulfide bonds.

Another embodiment of the invention comprises recombinant cells such as, for example, bacterial, mammalian or insect cells containing expressible protein sequences, wherein an f-met that is present at the N-terminus of the expressed protein is enzymatically removed. Preferred host cells include, but are not limited to, cells genetically engineered to shift the redox state of the cytoplasm to a more oxidative state, that contain and express an inducible MAP gene. Preferred cells include prokaryotic or eukaryotic cells such as, for example, E. coli cell expression systems, Baculovirus Expression System and other bacterial and/or eukaryotic cellular expression systems. Preferably the cells contain a protein expression system for expressing foreign or non-native sequences. Also preferable, the sequences to be expressed are comprised of an expression vector which contains one or more of an inducible promoter (e.g., auto-inducible preferably with specific media), a start codon (e.g., ATG), a ribosome binding site, and/or a modified sequence between ribosome binding site and ATG starting codon, or between start codon and the sequence to be expressed. Preferred modified sequences or spacer sequences include, for example, a number of nucleotides more or less than 9 (e.g., between 7 and 12 nucleotides), and preferably not 9 nucleotides.

Another embodiment of the invention is directed to recombinant protein and the expression of recombinant protein in E. coli or another host cell using an expression vector with an inducible promoter and/or a modified sequence between ribosome binding site and ATG starting codon, cells wherein an f-met that is present at the N-terminus of the recombinant protein that is enzymatically removed. Preferably, the expression vector includes the lactose/IPTG inducible promoter, preferably a tac promoter, and the sequence between ribosome binding site and ATG starting codon.

Another embodiment of the invention comprises an expression construction of nucleotide or amino acids sequences and with or without an enhancer region. Enhancers regions promote protein expression by adding one or more sequences that promote nucleic acid recognition for increased expression (e.g., start codon, enzyme binding site, translation or transcription factor binding site). Preferably, an enhancer of the invention contains a ribosome binding site with a start codon upstream of and with a coding sequence that differs from the coding sequence of the CRM protein.

Another embodiment of the invention is directed to recombinant protein purified according to the methods of invention. Purification preferably comprises heparin or heparin-like affinity chromatography. Presence of heparin binding site allows the use of heparin or heparin-like resins in the purification. Heparin-like resins include resins containing functional sulfate groups, such as dextran sulfate, e.g. Dextran sulfate (Sterogene), Capto Devirs (GE) or sulfate esters, e.g. Cellufine Sulfate (Asahi Kasei Bioprocess).

In a first step, crude E. coli extract may be clarified, for example, preferably by centrifugation or depth filtration. Optionally cleared lysate may be fractionated further, preferably by adding salts that have effect on protein solubility and salting out protein expressed. In the second step, clarified lysate or re-solubilized salted out fraction containing protein may be applied, for example, to anion exchange resin under conditions when protein is in flow through. In the third step, the flow through fraction containing protein may be applied to a column. Preferred column resins include, but are not limited to dextran sulfate resins, CELLUFINE™ resins (Chisso Corporation; chromatography gel), active sulfated resins, phosphate resins, or heparin or heparin-like resins. Preferably binding of protein to resin is performed in a low salt buffer and eluted in higher salt buffer, yielding highly purified protein. Preferred binding buffers contain, for example, one or more ionic reagents and/or reagents that increase conductivity, one or more chaotropic agents, NaCl, KCl, glycerol, isopropyl alcohol, ethanol, arginine, acetate, guanidine, urea, ATP, one or more mono-, di-, tri-, and/or poly-phosphates, sulfates or pyrophosphates, and combinations thereof. Preferred elution buffers contain, for example, higher concentration of one or more components of the binding buffer.

Other preferred purification methods include any one or combination of an anion exchange chromatography, hydrophobic interaction chromatography and/or Cibacron-Blue resin (CN 101265288A, U.S. Pat. No. 8,383,783). Purification method of the invention produce recombinant CRM protein (e.g., $CRM_{197}$) at high yields, as discussed herein, and with a purity level of greater than 80%, preferably greater than 85%, preferably greater than 90%, preferably greater than 95%, preferably greater than 99%, and preferably with an even greater purity.

Another embodiment of the invention is directed to proteins and peptides as well as portions and domains thereof, that can be manufactured according to the method of the invention. Proteins and peptides comprise, but are not limited to, for example, those proteins and peptides that can be cytoplasmically expressed without leader or tag sequences and at commercially significant levels according to the methods disclosed and described herein. Preferably, these proteins and peptides show proper folding upon expression in recombinant cells of the invention. Recombinant cells of the invention preferably show reduced activity of one or more disulfide reductase enzymes, preferable reduced activity of less than five disulfide reductase enzymes, preferable reduced activity of less than four disulfide reductase enzymes, and also preferable reduced activity of less than three disulfide reductase enzymes. Preferably expression of the proteins and peptides is increased in recombinant cells of the invention, but may be not reduced or not significantly reduced compared with expression in recombinant cell that does not have reduced activity of one or more disulfide reductase enzymes. Proteins and peptides that can be expressed in the methods disclosed herein include, but are not limited to, for example, tetanus toxin, tetanus toxin heavy chain proteins, diphtheria toxoid, CRM, tetanus toxoid, Pseudomonas exoprotein A, Pseudomonas aeruginosa toxoid, Bordetella pertussis toxoid, Clostridium perfringens toxoid, Escherichia coli heat-labile toxin B subunit, Neisseria meningitidis outer membrane complex, Hemophilus influenzae protein D, Flagellin Fli C, Horseshoe crab Haemocyanin, and fragments, derivatives, and modifications thereof.

Another embodiment of the invention is directed to portions and domains of proteins that are expressed thereof, fused genetically or by chemical modification or conjugation (e.g., carbodiimide, 1-cyanodimethylaminopyridinium tetrafluoroborate (CDAP)) with another molecule. Preferred other molecules are molecules such as, but not limited to, other proteins, peptides, lipids, fatty acids, saccharides and/or polysaccharides, including molecules that extend half-life (e.g., PEG, antibody fragments such as Fc fragments), stimulate and/or increase immunogenicity, or reduce or eliminate immunogenicity. Many proteins contains an N-terminal serine which useful for conjugation. Typical conjugation partner molecules include, but are not limited to polymers such as, for example, bacterial polysaccharides, polysaccharides derived from yeast, parasite and/or other microorganisms, polyethylene glycol (PEG) and PEG derivatives and modifications, dextrans, and derivatives, modified, fragments and derivatives of dextrans. One example of a conjugation compound is the polymer PEGASYS® (peginterferon alfa-2a). Other polymers, such as dextran, also increase the half-life of proteins and reduce immunogenicity of the conjugate partner. Polyners may be linked randomly or directed through site specitic conjugation such as, for example, by modification of N-terminal serines and/or threonines. Also, modifications may be used that selectively oxidize chemical groups for site specific conjugaton.

Another embodiment of the invention is directed to methods of producing a peptide containing a domain, fragment and/or portion comprising: expressing the peptide from a recombinant cell containing an expression vector that encodes the peptide, wherein the recombinant cell has a reduced activity of one or more disulfide reductase enzymes and the expression vector contains a promoter functionally linked to a coding region of the peptide, wherein the one or more disulfide reductase enzymes comprises one or more of an oxidoreductase, a dihydrofolate reductase, a thioredoxin reductase, or a glutathione reductase; and isolating the peptide expressed, wherein the peptide expressed is soluble and wherein the protein or peptide is expressed with an f-met at the N-terminus that is removed by a peptidase that is also expressed within the recombinant cell. Preferably the expression vector contains a ribosome binding site, an initiation codon, and, optionally, an expression enhancer region. Preferably the recombinant cell has a reduced activity of only one disulfide reductase enzyme, only two disulfide reductase enzymes, or two or more disulfide reductase enzymes. Preferably the reduced activity of the disulfide reductase enzymes results in a shift the redox status of the cytoplasm to a more oxidative state as compared to a recombinant cell that does not have reduced activity of one or more disulfide reductase enzymes. Preferably the recombinant cell is an E. coli cell or a derivative or strain of E. coli. Preferably the soluble peptide expressed comprises a natively folded protein or domain of the protein. The promoter may be a constitutive or inducible promoter, whereby expression comprises inducing the inducible promoter with an inducing agent. Preferred inducing agents include, for example, lactose (PLac), isopropyl β-D-1-thiogalactopyranoside (IPTG), substrates and derivative of substrates. In one preferred embodiment, the recombinant cell contains a second expression vector that preferably contains a coding region for a peptidase that preferably acts upon and selectively cleaves the peptide or protein expressed from the first expression vector. Preferably the second expression vector contains a second promoter functionally linked to the coding region and co-expressing comprises expressing the peptide and the peptidase. The two expression vectors may be induced together with the same inducing agent, or with different inducing agents, optionally at different times. Preferably the peptidase acts on and cleaves the peptide co-expressed with the peptidase. Preferably the peptide expressed is conjugated with a polymer such as, for example, dextran, a bacterial capsular polysaccharide, polyethylene glycol (PEG), or a fragment, derivative or modification thereof. Preferably the peptide expressed is coupled with a polymer which includes, for example, a polysaccharide, a peptide, an antibody or portion of an antibody, a lipid, a fatty acid, or a combination thereof.

Another embodiment of the invention comprises conjugates of proteins expressed and cleaved according to the disclosures herein including fragments, domains, and portions thereof as disclosed and described herein.

Another embodiment of the invention comprises fusion molecules of proteins included fragments, domains, and portions thereof as disclosed and described herein.

Another embodiment of the invention comprises a vaccine of proteins included fragments, domains, and portions thereof, as disclosed and described herein.

The following examples illustrate embodiments of the invention, but should not be viewed as limiting the scope of the invention.

EXAMPLES

Example 1 CRM197 Expressed in BL21

An *E. coli* strain was engineered to expresses soluble recombinant proteins containing disulfate bonds and effectively remove formyl-methaionine from the protein sequence. The strain was developed based on wildly use BL21 expression strain and deposited with the American Type Culture Collection. Shift from reducing to oxidative cytoplasmic environment was achieved by deletion of glutathione reductase gene. This single mutation allows disulfate bonds to be formed in the cytoplasm and does not affect cells vitality resulting in high cell density growth. In addition, BL21 gor- strain has additional copy of indigenous MAP. The coding sequence of *E. coli* MAP under control of inducible promoter was inserted in the place of deleted Gor locus of BL21 gor- to prevent further disruption of the genome. Having inducible promoter allows initiate expression of additional MAP gene at desired time and only when more AMP needed to effectively remove formyl-methionine from overexpressed recombinant protein. The tac-promoter was used as an inducible promoter for MAP. Thus, the expression of second MAP starts at the same time as expression of a recombinant protein when IPTG is used to induce its expression. Any other inducible promoter for MAP expression can be used.

The *E. coli* strain created is capable of producing soluble disulfide bonds containing proteins intracellularly in grams quantity per liter of cell culture and sufficiently remove N-terminal methionine resulting in the expression of native recombinant protein sequence.

Deletion of glutathione oxidoreductase used phage lambda Red recombination (Datsenko K. A., Wanner B. L., 2000). The parental strain used was *E. coli* BL21 (NEB, C2530H, lot #0191508). Plasmids used included CGSC, #140584, pKD46/MG1655 (7669), pKD3/BW25141/pKD3 (7631), pCP20/BT340 (7629).

Insertion deletion was used to replace Gor with sequences of chloramphenicol genes in between two Flipase recognition sites. Once bacteria with insertion deletion was identified by being Chloramphenicol resistant, the flipase gene in a plasmid would was introduced to remove the chloramphenicol gene. The final bacterial strain has one flipase recognition site remained and the Gor gene deletion. Cloning of MAP gene in the place of gor- locus. PCR primers were used to amplify MAP coding sequence from BL21 gor- genomic DNA. MAP cDNA was cloned into expression vector under control of tac promoter and T7 terminator. PCR primers were used to amplify fragment containing mAP with promoter and terminator. PCR primers were used to obtain linearized pKD3 sequence.

These two fragments were assembled to get ptac-mAP-pKD3 plasmid. MAP sequence was cloned upstream of marker gene chloramphenicol acetyl transferase (CAT) flanked by two flipase recognition target sequences. PCR primers were used to amplify DNA fragment containing tac promoter, mAP and CAT.

This fragment was transformed into pKD46 containing competent cells, plated on chloramphenicol containing LB plates, and incubated at 37 C overnight. The resulting colonies tested negative on amp plates were picked for PCR reactions with primers mAP insertion F and C1 mj (5'-gcccccgttttcaccatggg-3') to check for positive clones. This cell line was designated as BL21 ΔGor::(CAT, mAP). To remove the CAT marker gene, Pcp20 plasmid that contains a flipase gene was transformed into BL21 ΔGor::(CAT, mAP) and selected for amp resistant clones at 30 C. Positive clones were streaked and grew at 42 C overnight. The colonies did not grow on Ampicillin plates were selected and subjected to sequencing confirmation. Primers, Down Born and up Gor were used to do PCR on the genomic DNA of these colonies to obtain inserted sequence. These PCR products were then sequenced by using AP insert F and AP insert R primers to confirm the insertion of additional mAP at Gor locus.

CRM197 was produced in BL21 Gormet intracellularly and subjected to intact mass analysis. F-methionine was cleaved completely and 100% of purified protein has mature amino acids sequence lacking f-Met.

Two main species were observed in the NO21p114 CRM sample, which was consistent with a CRM monomer (58,542 Da) and without an N-terminal Met (reduced by 131 Da). One main species was observed in the NO21p221 CRM sample, which was consistent with a CRM monomer without an N-terminal Met (58,411 Da) (see Table I).

TABLE I

| | Non-Reduced CRM | | |
|---|---|---|---|
| | | Observed | |
| Species | Theoretical | NO21p114 | NO21p221 |
| CRM w/o Met | 58,409 Da | 58,411.6 Da | 58,411.4 Da |
| CRM w/Met | 58,540 Da | 58,542.2 Da | not observed |

Example 2 IL10 Expression in *E. coli*

IL10 was expressed in the *E. coli* strain. Peptide fragmentation by trypsin and LC-MS/MS was used to show that the protein had a molecular weight consistent with the f-Met being cleaved off the N-terminal and that the N-terminal peptide was the expected sequence.

Example 3 Site-Specifically Modification of a Protein 1-amino, 2-alcohol compounds with an N-terminal serine or threonine are selectively oxidized to an aldehyde by hypervalent iodine compounds (e.g., metaperiodate) (J. Pept. Sci. 2016; 22: 271-279) to create a protein with a unique N-terminal aldehyde. As there are few to no aldehydes naturally in proteins, this N-terminal aldehyde is selectively modified or functionalized.

Aminooxy, hydrazide and hydrazine reagents are particularly useful for functionalizing of aldehydes. Some examples of these reagents for modifying aldehydes are described in *Bioconjugate Chem.* 1990, 7, 96 and *Vaccine*, 2006, 24:716. Using standard genetic engineering methods, sequences for proteins containing N-terminal serine or threonine are introduced into *E. coli* bacteria for expression.

Proteins are synthesized in *E. coli* with f-Met as the starting amino acid which is normally cleaved off by proteases. However, high expression levels of heterologous proteins in *E. coli* can result in a significant fraction of the protein f-Met to be not fully trimmed, thus blocking the expected N-terminal serine or threonine. The N-terminal f-Met is efficiently cleaved off and thus allows for proteins to be expressed so that the N-terminal serine or threonine is available for facile oxidation.

Example 4 Terminal Modification of a Protein $CRM_{197}$ is expressed as described in Example 1, but with an N-terminal serine or threonine. Oxidation of the N-terminal serine or threonine is carried out as generally described in Bioconjugate Chem. 1994, 5, 636-646. The $CRM_{197}$ is purified and prepared at 5 mg/ml in sodium phosphate buffer, pH 6.8, treated with a 5× molar excess of sodium metaperiodate for 8 minutes and then quenched with a 10× molar excess of glycerol. The N-terminal oxidized protein is desalted, concentrated to 5 mg/ml, pH 8 HEPES. The protein is then reacted with an aminooxy reagent such as an 1-(Aminooxy)-4-[(3-nitro-2-pyridyl)dithio]butane (Bioconjugate Chem. 1990, 7, 96-99), optionally in the presence of a mild reducing agent such as sodium cyanoborohydride. Following purification, the product is a protein with the N-terminal modified with a thiol-pyridyl disulfide. The disulfide is reduced with a low concentration of a reducing agent (e.g., DTT) to prepare $CRM_{197}$ with a single terminal thiol. The monothiol protein is then reacted with an antigen or other molecule containing a suitable electrophilic group, for example, a polysaccharide functionalized with maleimide groups.

The monothiol is further modified by reaction with thiol-reactive reagents. The thiol is converted to a maleimide group by the addition of an excess of a di-maleimide reagent. The N-terminal aldehyde is labeled with useful groups, including click reagents, biotin, fluorescent compounds, maleimides, bromoacetyl groups and more. A catalyst, such as an analine or 4-amino phenylalanine is used to promote oxime formation (J. Pept. Sci. 2016; 22: 271-279). The oxime can optionally be reduced using a reagent such as sodium cyanoborohydride. The reducing reagent may be present during the oximation reaction if it does not affect the aldehyde or may be added at the conclusion of the reaction. Hydrazide and hydrazine reagents may also be reacted with the oxidized N-terminal amino acid instead of aminooxy reagents.

Example 5 Bacterial Strain with Elevated Activity of Methionine Aminopeptidase (MAP) that Forms Disulfide Bonds in the Cytoplasm

*E. coli* strains used to express recombinant proteins can have a reducing intracellular environment preventing formation of disulfide bonds. However, many proteins require disulfide bonds for proper folding, solubility, and function. Expression in the *E. coli* reducing cytoplasm leads to insoluble expression of recombinant proteins (e.g., inclusion bodies). These proteins must then be refolded, a frequently challenging and largely unsuccessful process. To achieve soluble production of such proteins in *E. coli*, expression can be directed to the periplasm.

Periplasmic expression results in low expression yield due to the limited capacity of *E. coli* secreted pathways. Commercially available strains of *E. coli* are available that contain multiple genes knocked out to create an oxidizing intracellular environment. Such commercially available *E. coli* strains include SHuffle® (New England Bio) and Origami™ (Millipore). Neither of these strains are well-suited for recombinant protein manufacturing due to impaired growth and low cell mass accumulation.

An *E. coli* strain (GorMet) was created that contains an oxidizing intracellular environment and is capable of producing soluble cytoplasmic proteins, including ones containing disulfide bonds. A property of the strain is that it not crippled and can generate large amounts of cell mass and thus is highly suitable for recombinant protein manufacturing.

In contrast to previous *E. coli* strains with an oxidative intracellular environment, the GorMet strain has only a single gene deletion, of glutathione reductase to shift intracellular environment of *E. coli* cells to oxidative state to allow disulfide formation. Surprisingly, this single gene deletion creates a suitable oxidative intracellular environment which does not affect cell growth, allowing the expression of grams of recombinant proteins per liter of cell culture Deletion of glutathione reductase from BL21 genome 1. PCR was used to introduce upstream and downstream sequences of the BL21 Gor gene to 3' and 5' of a chloramphenicol acetyl transferase gene framed with Flippase recognition sites, respectively.
2. BL21 cells were transformed with a temperature sensitive plasmid expressing red recombinase and induced the recombinase activity.
3. The cells resulting from step 2 were transformed with the step 1 PCR product to replace Gor gene with chloramphenicol acetyl transferase gene.
4. Positive clones were selected by chloramphenicol resistance.
5. The plasmid containing Red recombinase was removed by growing the transformed BL21 cells at 42° C.
6. The transformed temperature sensitive plasmid containing flippase was used to remove the chloramphenicol acetyl transferase gene from the genome.
7. The cells of step 6 were grown at 42° C. to remove plasmid containing flippase.
8. Sequencing was performed to confirm the gene insertion at the correct locus.

This created a BL21 *E. coli* strain with an oxidative intracellular environment.

A substantial amount of the recombinant protein produced in a microorganism contains methionine as the first amino acid. As Met is not a part of mature protein sequence, this is not desirable for many proteins. Expression of recombinant proteins (heterologous) in *E. coli* initiates at the coding sequence of the protein, the ATG codon. This is translated to formyl-methionine (N-terminal Met). During the intracellular expression of proteins, the N-terminal Met is excised by endogenous *E. coli* methionine aminopeptidase (or peptidases). This process is not efficient even if the residue adjacent to the N-terminal methionine is optimal for cleavage due to overexpression of the protein and limited amount of MAP.

Present methods to cleave formyl-methionine include in vitro treatment with recombinant MAP or adding the MAP coding sequence to the expression vector in order to coexpress it with the recombinant protein. All these methods are time consuming and costly as a new expression vector must be created and optimized for each new recombinant protein.

In this example, the MAP gene was integrated into the genome of this *E. coli* strain, with MAP expression controlled by a promoter. Recombinant proteins expressed had the formyl-methionine removed from their N terminus such that no or very low levels of N-terminal methionine were present on expressed proteins, and removal did not the disulfide bonds formation for solubility and function, in the cytoplasm of *E. coli*. Recombinant proteins expressed in this strain were soluble, have their disulfide bonds correctly formed and possess the native sequence without an N-terminal methionine.

The strain BL21 *E. coli* gor⁻ was engineering further by inserting an extra copy of bacterial methionine aminopeptidase (MAP) under the control of an inducible promoter into the gor⁻ locus.

Method for MAP gene insertion:
1. PCR was used to obtain a DNA fragment containing the coding sequence of methionine aminopeptidase (MAP) from *E. coli* BL21 genome.
2. The MAP coding sequence was cloned into a bacterial expression vector under the control of the tac promoter.
3. PCR was used to amplify the MAP sequence along with the promoter and terminator using the plasmid from the step 2 as a template.
4. PCR was used to add the methionine aminopeptidase gene with promoter and terminator from step 3 upstream of the Chloramphenicol acetyl transferase promoter on pKD3 vector.
5. PCR was used to obtain a gene cassette that contained the methionine aminopeptidase plus Chloramphenicol acetyl transferase gene with their respective promoters and terminators with additional sequences of upstream and downstream glutathione reductase gene deletion locus (gor-).
6. Red Recombineering was performed to insert the gene cassette made in step 5 into the Gor locus in BL21 Gor-.
7. Flippase was used to remove the Chloramphenicol acetyl transferase gene from the genome.
8. Sequencing was performed to confirm that the gene insertion occurred at the correct locus.

With an inducible promoter (Tac), the initiation of expression of the additional MAP gene at the desired time and only when more AMP needed to effectively remove the formyl-methionine from the N-terminal of the overexpressed recombinant protein. The expression of the second MAP starts at the same time as the expression of a recombinant protein when IPTG is the inducer. Any other inducible promoter for MAP expression can be used.

Example 6. Expression Genetically Detoxified Diphtheria Mutant $CRM_{197}$ in the Gormet Strain and in the Gor- *E. coli* Strain The expression level was greater than about 2 g per liter fermenter cell culture for both strains, indicating the co-expression of the MAP did not significantly affect the expression of the CRM197. Purified CRM197 for each strain was analyzed by mass spectrometry (see Table II).

TABLE II

| Major species | With N-met | Without N-met |
|---|---|---|
| Expression system | 58,540 | 58,409 |
| Gor | 58,541 | |
| GorMet | | 58,411 |

It is seen that the major species for CRM197 expressed in the GorMet strain had an appropriate molecular weight for the N terminal Met being cleaved, whereas expression in the Gor strain resulted CRM197 with an N-terminal methionine.

Example 7. Expression of Cytokine IL10 from Epstein-Barr Virus in the Gormet Strain IL10 was expressed soluble intracellularly. Purified IL10 was subjected to mass spectrometry analysis. Following enzymatic digestion with trypsin, the sample was analyzed by LC-MS/MS. The IL10 amino acid sequence did not contain N-terminal methionine.

Example 8. Use of GorMet Strain to Produce Proteins that can be Site Specifically Modified at the N-Terminal It can be desirable to site-specifically modify a protein. 1-amino, 2-alcohol compounds, such as N-terminal serine or threonine can be selectively oxidized to an aldehyde (J. Pept. Sci. 2016; 22: 271-279) to create a protein with a unique N-terminal aldehyde. As there are few to no aldehydes naturally in proteins, this N-terminal aldehyde can then be selectively modified or functionalized. Aminooxy, hydrazide and hydrazine reagents are particularly useful for functionalizing of aldehydes. Some examples of these reagents for modifying aldehydes are described in *Bioconjugate Chem.* 1990, 7, 96 and Vaccine, 2006, 24:716. Using standard genetic engineering methods, sequences for proteins containing 1-amino, 2-alcohol amino acids can be introduced into genes being expressed in *E. coli* bacteria. These N-terminal amino acids can then be oxidized to create an aldehyde for site specific modification. However, if the N-terminal Met is not efficiently removed, the 1-amino,2-alcohol group cannot be easily selectively oxidized.

The *E. coli* strains created provide a method for efficiently cleaving off the N-terminal Met and thus allows for proteins to be expressed so that the N-terminal serine or threonine is available for facile oxidation. A gene for expressing a protein with an N-terminal 1-amino, 2-alcohol amino acid was introduced into the GorMet strain, expressed and purified. The purified protein had the N-terminal Met cleaved, leaving the 1-amino, 2-alcohol amino acid on the N-terminal. Oxidation of this amino acid was carried out as generally described in Bioconjugate Chem. 1994, 5, 636-646. The protein, containing an N-terminal aldehyde was further reacted.

A gene containing the CRM197 sequence plus an N-terminal serine or threonine was introduced into the GorMet E. coli as described. The expressed CRM197 has essentially all of the Met cleaved by the MAP so that the protein has an N-terminal serine or threonine. The $CRM_{197}$ was purified and prepared at 5 mg/ml in sodium phosphate buffer, pH 6.8, treated with a 5× molar excess of sodium metaperiodate for 8 minutes and then quenched with a 10× molar excess of glycerol. The N-terminal oxidized protein was desalted, concentrated to 5 mg/ml, pH 8 HEPES. This protein was reacted with the aminooxy reagent 1-(Aminooxy)-4-[(3-nitro-2-pyridyl)dithio]butane (Bioconjugate Chem. 1990, 7, 96-99). This was performed in the presence of a mild reducing agent (sodium cyanoborohydride), which is optional. Following purification, the product produced was a protein with the N-terminal modified with a thiol-pyridyl disulfide. The disulfide was reduced with a low concentration of a reducing agent (DTT, although any would suffice) to prepare $CRM_{197}$ with a single terminal thiol. The monothiol protein was reacted with an antigen containing a suitable electrophilic group, a polysaccharide functionalized with maleimide groups.

The monothiol was modified by reaction with thiol-reactive reagents. The thiol was converted to a maleimide group by the addition of an excess of a di-maleimide reagent. The N-terminal aldehyde was labeled with a useful group (e.g., click reagents, biotin, fluorescent compounds, maleimides, bromoacetyl groups and many more). As such, it can be reacted with hydrazide, hydrazine, aminooxy groups or other reagents known to selectively react with aldehydes. The protein with an N-terminal aldehyde can be reacted with a suitably modified protein, for example a hydrazide derivatized protein, polymer, polysaccharide, oligosaccharide or peptide. It may also be reacted with suitably modified surfaces, including but not limited to, beads, chromatography resins or membranes. A catalyst, such as an analine or 4-amino phenylalanine can be used to promote oxime formation (J. Pept. Sci. 2016; 22: 271-279). The oxime can be reduced using a reagent such as sodium cyanoborohydride. The reducing reagent may be present during the oximation reaction if it does not affect the aldehyde or may be added at the conclusion of the reaction. Hydrazide and hydrazine reagents may also be reacted with the oxidized N-terminal amino acid instead of aminooxy reagents.

Example 9 Deletion of Glutathione Reductase from E. coli BL21 Genome

PCR was used to introduce upstream and downstream sequences of the BL21 Gor gene to 3' and 5' of a chloramphenicol acetyl transferase gene framed with Flippase recognition sites, respectively. BL21 cells were transformed with a temperature sensitive plasmid expressing red recombinase and induced the recombinase activity. The resulting cells were transformed with the PCR product to replace Gor gene with chloramphenicol acetyl transferase gene. Positive clones were selected by chloramphenicol resistance. The plasmid containing Red recombinase was removed by growing the transformed BL21 cells at 42° C. A transformed temperature sensitive plasmid containing flippase was used to remove the chloramphenicol acetyl transferase gene from the genome. The resulting cells were grown at 42° C. to remove plasmid containing flippase. Sequencing was performed to confirm the gene insertion at the correct locus. This created a BL21 E. coli strain (BL21 E. coli gor) with an oxidative intracellular environment. The resulting strain BL21 E. coli gor was engineering further by inserting an extra copy of bacterial methionine aminopeptidase (MAP) under the control of an inducible promoter into the gor locus.

Example 10 MAP Gene Insertion

PCR was used to obtain a DNA fragment containing the coding sequence of methionine aminopeptidase (MAP) from E. coli BL21 genome. The MAP coding sequence was cloned into a bacterial expression vector under the control of the tac promoter. PCR was used to amplify the MAP sequence along with the promoter and terminator using the plasmid from the step 2 as a template. PCR was used to add the methionine aminopeptidase gene with promoter and terminator upstream of the Chloramphenicol acetyl transferase promoter on pKD3 vector. PCR was used to obtain a gene cassette that contained the methionine aminopeptidase plus Chloramphenicol acetyl transferase gene with their respective promoters and terminators with additional sequences of upstream and downstream glutathione reductase gene deletion locus (gor-). Red Recombineering was performed to insert the gene cassette into the Gor locus in BL21 Gor-. Flippase was used to remove the Chloramphenicol acetyl transferase gene from the genome. Sequencing was performed to confirm that the gene insertion occurred at the correct locus. Having an inducible promoter allowed the initiation of expression of the additional MAP gene at the desired time when more AMP needed to effectively remove the formylmethionine from the N-terminal of the overexpressed recombinant protein. The tac-promoter was used as an inducible promoter for MAP. Thus, the expression of the second MAP will start at the same time as the expression of a recombinant protein if IPTG is used to induce its expression. Any other inducible promoter for MAP expression can be used.

Example 11 Expression Genetically Detoxified Diphtheria Mutant CRM197

Expression genetically detoxified diphtheria mutant $CRM_{197}$ in the GorMet strain and in the Gor- E. coli strain. The expression level was >2 g per liter fermenter cell culture for both strains, indicating the co-expression of the MAP did not significantly affect the expression of the $CRM_{197}$. Purified $CRM_{197}$ for each strain was analyzed by mass spectrometry (Table 1). Lot NO21p114 was expressed in the Gor- strain and Lot NO21p221 was expressed in the GorMet strain, as shown in Table 1.

TABLE 1

| | Non-reduced CRM197 (n = 3, 1 SD) | | |
|---|---|---|---|
| | | Observed | |
| Species | Theoretical | NO21p114 | NO21p221 |
| CRM (w/out Met) | ~58,409 Da | 58,411.6 ± 0.4 Da | 58,411.4 ± 0.0 Da |
| CRM (with Met) | ~58,540 Da | 58,542.2 ± 0.1 Da | not observed |

Example 12 Expression of Cytokine IL10 from Epstein-Barr Virus in the Gormet Strain IL10 was cloned and expressed soluble intracellularly in GorMet E. coli. A metal affinity tag was included on C-terminal to facilitate purification. IL10, purified by IMAC and ion exchange chromatography was subjected to mass spectrometry analysis. Following enzymatic digestion with trypsin, the sample was analyzed by LC-MS/MS. The analysis found that IL10 expressed did not contain N-terminal methionine.

Example 13 Proteins Specifically Modified at the N-Terminal with the GorMet Strain Often it is desirable to site-specifically modify a protein. 1-amino, 2-alcohol compounds, such as N-terminal serine or threonine can be selectively oxidized to an aldehyde (J. Pept. Sci. 2016; 22: 271-279) to create a protein with a unique N-terminal aldehyde. As there are few to no aldehydes naturally in proteins, this N-terminal aldehyde can then be selectively modified or functionalized. Aminooxy, hydrazide and hydrazine reagents are particularly useful for functionalizing of aldehydes. Some examples of these reagents for modifying aldehydes are described in Bioconjugate Chem. 1990, 7, 96 and Vaccine, 2006, 24:716. Using standard genetic engineering methods, sequences for proteins containing 1-amino, 2-alcohol amino acids can easily be introduced into genes being expressed in E. coli bacteria. These N-terminal amino acids can then be oxidized to create an aldehyde for site specific modification. However, when the N-terminal Met is not efficiently removed, the 1-amino,2-alcohol group cannot be easily selectively oxidized. The efficient cleavage of the N-terminal Met allows for proteins to be expressed so that the N-terminal serine or threonine is available for facile oxidation.

A gene for expressing a protein with an N-terminal 1-amino, 2-alcohol amino acid was introduced into the GorMet strain, expressed and purified. The purified protein has the N-terminal Met cleaved, leaving the 1-amino, 2-alcohol amino acid on the N-terminal Oxidation of this amino acid is carried out as generally described in Bioconjugate Chem. 1994, 5, 636-646. The protein, containing an N-terminal aldehyde can then be further reacted.

As an example, a gene containing the $CRM_{197}$ sequence plus an N-terminal serine or threonine is introduced into the GorMet E. coli described. The expressed $CRM_{197}$ has essentially all of the Met cleaved by the MAP so that the protein has an N-terminal serine or threonine. The $CRM_{197}$ is purified and prepared at 5 mg/ml in sodium phosphate buffer, pH 6.8, treated with a 5× molar excess of sodium metaperiodate for 8 minutes and then quenched with a 10× molar excess of glycerol. The N-terminal oxidized protein is desalted, concentrated to 5 mg/ml, pH 8 HEPES. This protein is then reacted with an aminooxy reagent such as an 1-(Aminooxy)-4-[(3-nitro-2-pyridyl)dithio]butane (Bioconjugate Chem. 1990, 7, 96-99), optionally in the presence of a mild reducing agent such as sodium cyanoborohydride. Following purification, the product is a protein with the N-terminal modified with a thiol-pyridyl disulfide. The disulfide is easily reduced with a low concentration of a reducing (e.g., DTT) to prepare $CRM_{197}$ with a single terminal thiol. The monothiol protein is then reacted with an antigen or other molecule containing a suitable electrophilic group, for example, a polysaccharide functionalized with maleimide groups.

The monothiol can be further modified by reaction with thiol-reactive reagents. For example, the thiol can be converted to a maleimide group by the addition of an excess of a di-maleimide reagent. The N-terminal aldehyde can be labeled with many useful groups, including click reagents, biotin, fluorescent compounds, maleimides, bromoacetyl groups and many more, and reacted with hydrazide, hydrazine, aminooxy groups or other reagents known to selectively react with aldehydes.

The protein with an N-terminal aldehyde is then reacted with a suitably modified protein, for example a hydrazide derivatized protein, polymer, polysaccharide, oligosaccharide or peptide. It may also be reacted with suitably modified surfaces, including but not limited to, beads, chromatography resins or membranes.

A catalyst, such as an analine or 4-amino phenylalanine can be used to promote oxime formation ((J. Pept. Sci. 2016; 22: 271-279). The oxime can optionally be reduced using a reagent such as sodium cyanoborohydride. The reducing reagent may be present during the oximation reaction if it does not affect the aldehyde or may be added at the conclusion of the reaction. Hydrazide and hydrazine reagents may also be reacted with the oxidized N-terminal amino acid instead of aminooxy reagents.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where used, is intended to include the terms consisting and consisting essentially of. Furthermore, the terms comprising, including, containing and the like are not intended to be limiting. It is intended that the specification and examples be considered exemplary only with the true scope and spirit of the invention indicated by the following claims.

The invention claimed is:

1. A method of producing a peptide comprising:
expressing the peptide in a recombinant cell containing a gene that encodes a peptidase enzyme,
wherein the gene that encodes the peptidase enzyme is integrated into the genome of the recombinant cell,
wherein the recombinant cell has a reduced activity of one or more disulfide reductase enzymes,
wherein the reduced activity of one or more disulfide reductase enzymes results in a shift in the redox status of the cytoplasm to a more oxidative state as compared to a recombinant cell that does not have reduced activity of one or more disulfide reductase enzymes, and
wherein the peptide contains an N-terminal methionine;
expressing the peptidase enzyme which removes the N-terminal methionine from the peptide; and
isolating the peptide.

2. The method of claim 1, wherein the peptide comprises tetanus toxin, tetanus toxin heavy chain proteins, diphtheria toxoid, tetanus toxoid, Pseudomonas exoprotein A, Pseudomonas aeruginosa toxoid, Bordetella pertusis toxoid, Clostridium perfringens toxoid, Escherichia coli (E. coli) heat-labile toxin B subunit, Neisseria meningitidis outer membrane complex, Hemophilus influenzae protein D, Flagellin Fli C, Horseshoe crab or Haemocyanin.

3. The method of claim 1, wherein the recombinant cell has a reduced activity of only one disulfide reductase enzyme.

4. The method of claim 1, wherein the recombinant cell has a reduced activity of two or more disulfide reductase enzymes.

5. The method of claim 1, wherein the one or more disulfide reductase enzymes comprises one or more of an oxidoreductase, a dihydrofolate reductase, a thioredoxin reductase, or a glutathione reductase.

6. The method of claim 1, wherein the recombinant cell is an *E. coli* cell or a derivative or strain of *E. coli*.

7. The method of claim 1, wherein the gene that encodes the peptide contains a first inducible promoter and/or the gene that encodes the peptidase enzyme contains a second inducible promoter.

8. The method of claim 1, wherein the gene that encodes the peptide contains a first inducible promoter and the gene that encodes the peptidase enzyme contains a second inducible promoters and the first and second inducible promoters are the same.

9. The method of claim 1, wherein isolating comprises chromatography.

10. The method of claim 9, wherein the chromatography comprises a sulfate resin, a gel resin, an active sulfated resin, a phosphate resin, a heparin resin or a heparin-like resin.

11. The method of claim 1, further comprising conjugating or coupling the isolated peptide with a chemical compound.

12. The method of claim 11, wherein the chemical compound comprises a polysaccharide, a polymer, a polyethylene glycol, a derivative of polyethylene glycol, a peptide, an antibody or portion of an antibody, a lipid, a fatty acid, or a combination thereof.

13. The method of claim 1, wherein the peptide is oxidized with an oxidizing agent.

14. The method of claim 13, wherein the oxidizing agent comprises a hydrazide, a hydrazine, an aminooxy group, N-terminal 1-amino, 2-alcohol amino acid, or a combination thereof.

15. A method of producing a peptide containing disulfide bonds comprising:
    expressing the peptide in a recombinant cell containing a gene that encodes a peptidase enzyme,
        wherein the peptide is encoded in an expression vector,
        wherein the gene that encodes the peptidase enzyme is integrated into the genome of the recombinant cell,
        wherein the recombinant cell has a reduced activity of one or more disulfide reductase enzymes,
        wherein the recombinant cell is *E. coli*, and
        wherein the peptide contains an N-terminal methionine;
    expressing the peptidase enzyme which removes the N-terminal methionine from the peptide; and
    isolating the peptide from within the cytoplasm of the recombinant cell, wherein the peptide isolated is soluble.

16. The method of claim 15, wherein the peptide comprises tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* (*E. coli*) heat-labile toxin B subunit, *Neisseria meningitidis* outer membrane complex, Hemophilus influenzae protein D, Flagellin Fli C, Horseshoe crab or Haemocyanin.

17. The method of claim 15, wherein the recombinant cell has a reduced activity of only one disulfide reductase enzyme and the one disulfide reductase enzymes comprises an oxidoreductase, a dihydrofolate reductase, a thioredoxin reductase, or a glutathione reductase.

18. The method of claim 15, wherein the gene that encodes the peptide contains a first inducible promoter and/or the gene that encodes the peptidase enzyme contains a second inducible promoter.

19. The method of claim 15, wherein the gene that encodes the peptide contains a first inducible promoter and the gene that encodes the peptidase enzyme contains a second inducible promoters and the first and second inducible promoters are the same.

20. The method of claim 15, wherein isolating comprises chromatography.

21. A method of producing a protein comprising:
    providing an expression vector that encodes the protein, wherein the protein contains one or more sulfide linkages;
    expressing the expression vector in a recombinant cell that has a reduced activity of a disulfide reductase enzyme which results in a shift in the redox status of the cytoplasm of the recombinant cell to a more oxidative state as compared to a recombinant cell that does not have reduced activity of the disulfide reductase enzyme; and
    isolating the protein expressed by the recombinant cell wherein the protein expressed is correctly folded and soluble in the cytoplasm.

22. The method of claim 21, wherein the protein expressed is selected from the group consisting of tetanus toxin, tetanus toxin heavy chain proteins, diphtheria toxoid, tetanus toxoid, *Pseudomonas* exoprotein A, *Pseudomonas aeruginosa* toxoid, *Bordetella pertusis* toxoid, *Clostridium perfringens* toxoid, *Escherichia coli* (*E. coli*) heat-labile toxin B subunit, *Neisseria meningitidis* outer membrane complex, Hemophilus influenzae protein D, Flagellin Fli C, Horseshoe crab Haemocyanin, and a domain thereof.

23. The method of claim 21, wherein the one disulfide reductase enzyme comprises glutathione reductase.

24. The method of claim 21, wherein the reduced activity of the disulfide reductase enzyme does not affect vitality of the recombinant cell or growth of a population of recombinant cells.

25. The method of claim 21, wherein the recombinant cell is an *E. coli* cell or a derivative or strain of *E. coli*.

26. The method of claim 21, wherein the expression vector contains a ribosome binding site, an initiation codon, and/or an expression enhancer region.

27. The method of claim 21, wherein the expression vector contains an inducible promoter and expressing the protein comprises inducing the inducible promoter with an inducing agent.

28. The method of claim 21, wherein 200 mg or more of the expressed protein is isolated from one liter of recombinant cells.

29. The method of claim 21, wherein 500 mg or more of the expressed protein is isolated from one liter of recombinant cells.

30. The method of claim 21, wherein 1,000 mg or more of the expressed protein is isolated from one liter of recombinant cells.

31. The method of claim 21, wherein 2,000 mg or more of the expressed protein is isolated from one liter of recombinant cells.

32. The method of claim 21, wherein isolating comprises chromatography.

33. The method of claim 32, wherein the chromatography comprises a sulfate resin, a gel resin, an active sulfated resin, a phosphate resin, a heparin resin or a heparin-like resin.

34. The method of claim 21, further comprising conjugating or coupling the isolated protein with a chemical compound.

35. The method of claim 34, wherein the chemical compound comprises a polysaccharide, a polymer, a polyethylene glycol, a derivative of polyethylene glycol, a peptide, an antibody or portion of an antibody, a lipid, a fatty acid, or a combination thereof.

* * * * *